(12) United States Patent
Pendekanti et al.

(10) Patent No.: US 7,431,720 B2
(45) Date of Patent: Oct. 7, 2008

(54) MULTI-FUNCTION CLAMPING DEVICE WITH STAPLER AND ABLATION HEADS

(75) Inventors: Rajesh Pendekanti, Bridgewater, NJ (US); Shailendra K. Parihar, Coopersburg, PA (US); Chung-Yih Ho, Belle Meade, NJ (US)

(73) Assignee: Ethicon, Inc., Somerville, NJ (US)

( * ) Notice: Subject to any disclaimer, the term of this patent is extended or adjusted under 35 U.S.C. 154(b) by 583 days.

(21) Appl. No.: 10/721,303

(22) Filed: Nov. 25, 2003

(65) Prior Publication Data
US 2005/0113821 A1    May 26, 2005

(51) Int. Cl.
*A61B 18/12* (2006.01)
(52) U.S. Cl. .......................... 606/41; 606/142
(58) Field of Classification Search .......... 606/37–42, 606/45–52, 142–143, 205–209, 27, 28; 227/175.1, 227/179.1, 180.1, 19, 176.1, 178.1
See application file for complete search history.

(56) References Cited

U.S. PATENT DOCUMENTS

| | | | |
|---|---|---|---|
| 4,566,620 A * | 1/1986 | Green et al. | 227/19 |
| 5,258,006 A * | 11/1993 | Rydell et al. | 606/205 |
| 5,389,098 A * | 2/1995 | Tsuruta et al. | 606/41 |
| 5,403,312 A | 4/1995 | Yates et al. | |
| 5,433,721 A * | 7/1995 | Hooven et al. | 606/143 |
| 5,439,155 A * | 8/1995 | Viola | 227/176.1 |
| 5,452,836 A | 9/1995 | Huitema et al. | |
| 5,465,894 A | 11/1995 | Clark et al. | |
| 5,605,272 A | 2/1997 | Witt et al. | |
| 5,665,085 A | 9/1997 | Nardella | |
| 5,688,270 A * | 11/1997 | Yates et al. | 606/51 |
| 5,716,366 A | 2/1998 | Yates | |
| 5,735,848 A | 4/1998 | Yates et al. | |
| 5,772,597 A | 6/1998 | Goldberger et al. | |
| 5,876,401 A | 3/1999 | Schulze et al. | |
| 5,954,259 A * | 9/1999 | Viola et al. | 227/176.1 |
| 6,032,849 A | 3/2000 | Mastri et al. | |
| 6,126,665 A | 10/2000 | Yoon | |
| 6,187,002 B1 | 2/2001 | Long et al. | |
| 6,402,008 B1 | 6/2002 | Lucas | |
| 6,517,536 B2 * | 2/2003 | Hooven et al. | 606/41 |
| 6,638,285 B2 * | 10/2003 | Gabbay | 606/151 |
| 6,698,643 B2 * | 3/2004 | Whitman | 227/180.1 |
| 6,821,273 B2 * | 11/2004 | Mollenauer | 606/28 |
| 2004/0116921 A1 | 6/2004 | Sherman et al. | |
| 2005/0021026 A1 * | 1/2005 | Baily | 606/51 |
| 2005/0090817 A1 * | 4/2005 | Phan | 606/41 |

* cited by examiner

*Primary Examiner*—Roy D Gibson

(57) ABSTRACT

Stapler and ablation clamping heads can be interchangeably coupled to a hand-operated actuation mechanism using a quick connect/quick release coupling. In the actuation mechanism, a first user-operable lever controls clamping of the jaws of either head, while a second user-operable lever controls the firing of staples in the stapler head. A removable staple holder may be used with the stapler head to allow easy reloading of staples as well as the use of different sizes and type of staples. A corresponding removable anvil may be used as well. A removable electrode holder may be used with the ablation head to allow the use of different electrode configurations. Moreover, a removable electrode holder may be used over the jaws of a stapler head as an overlay.

24 Claims, 15 Drawing Sheets

MULTI-FUNCTION CLAMPING DEVICE WITH STAPLER AND ABLATION HEADS

BACKGROUND OF THE INVENTION

1. Field of the Invention

The invention relates to the field of medical instruments, and more particularly, to a dual function clamping device with interchangeable stapler and ablation heads.

2. Description of the Related Art

Various surgical procedures are performed using separate stapler and ablation devices. For example, atrial fibrillation (AF) is the most common form of arrhythmia, affecting more than 2 million people annually. AF is treated by the Maze procedure, which is a surgical intervention that interrupts the circular electrical patterns in the heart. Tissue in both atria are scarred or ablated to stop the formation and conduction of errant electrical impulses and/or to channel the normal electrical impulse in one direction from the top of the heart to the bottom of the heart. This procedure requires a device that can create ablation lines using RF or ultrasound energy or any other energy. Additionally, concurrent with a Maze-type procedure, the left atrial appendage may be closed to prevent emboli that might form within the appendage while the heart is fibrillating from exiting the appendage pouch and causing a subsequent stroke. This procedure requires a device with jaws that can clamp the atrial appendage and deliver staples to close the appendage.

The use of separate devices for stapling and ablating is inefficient and time consuming, however, and results in increased costs, storage requirements, sterilizing needs, and other maintenance needs. Additionally, separate stapling devices may be required to deliver different sizes or types of staples. Separate ablation devices may be required as well to provide different electrode configurations.

BRIEF SUMMARY OF THE INVENTION

The present invention addresses the above and other issues.

In one aspect of the invention, an actuation mechanism is provided for replaceable or exchangeable clamping heads. The actuation mechanism provides a first actuation member for controlling a clamping head that can be removably coupled to the actuation mechanism. For example, when a clamping head including a stapler is coupled to the actuation mechanism, the first actuation member may control the clamping of the clamping head. The actuation mechanism further includes an electrical supply line for electrically energizing an electrically-energizable clamping ablation head. Any other type of head that is electrically-energizable may be used. The electrically-energizable head need not be a clamping head. Different clamping heads can be easily and quickly interchanged on the actuation mechanism using a quick connect/quick release coupling, such as a ball and socket coupling.

In another aspect of the invention, a clamping ablation device provides both clamping and ablation functions.

A further embodiment of a clamping ablation head provides an electrode holder that is removably receivable by a jaw.

An ablation head includes a pair of electrode holders that are removably receivable by first and second jaws of the ablation head. A pair of such removable electrode holders may also be provided, where one of the electrodes acts as a cathode electrode, and the other acts as an anode electrode.

In another aspect of the invention, a stapler head is provided that can be coupled to an actuation mechanism, where a staple holder is removably receivable by a second jaw of the stapler head to allow easy reloading of staples as well as loading of different staple sizes and types.

In yet another aspect of the invention, a combination stapler and ablation head is provided, where a first jaw of the head includes an anvil, a second jaw includes a staple driving mechanism, and an electrode holder is removably receivable by one of the jaws, e.g., as an overlay, such that an electrical contact of the electrode is electrically coupled to an electrical contact of one of the jaws.

In yet another aspect of the invention, a clamping device includes a handle assembly, an elongated body with first and second actuation members, an electrical supply line, a coupling at the distal end of the elongated body, and a clamping head actuable by the first and second actuation members.

BRIEF DESCRIPTION OF THE DRAWINGS

The advantages and benefits of the current invention will be made apparent through the following descriptions and accompanying figures, where like reference numerals refer to the same features across the various drawings.

DETAILED DESCRIPTION OF THE INVENTION

Figure 1:
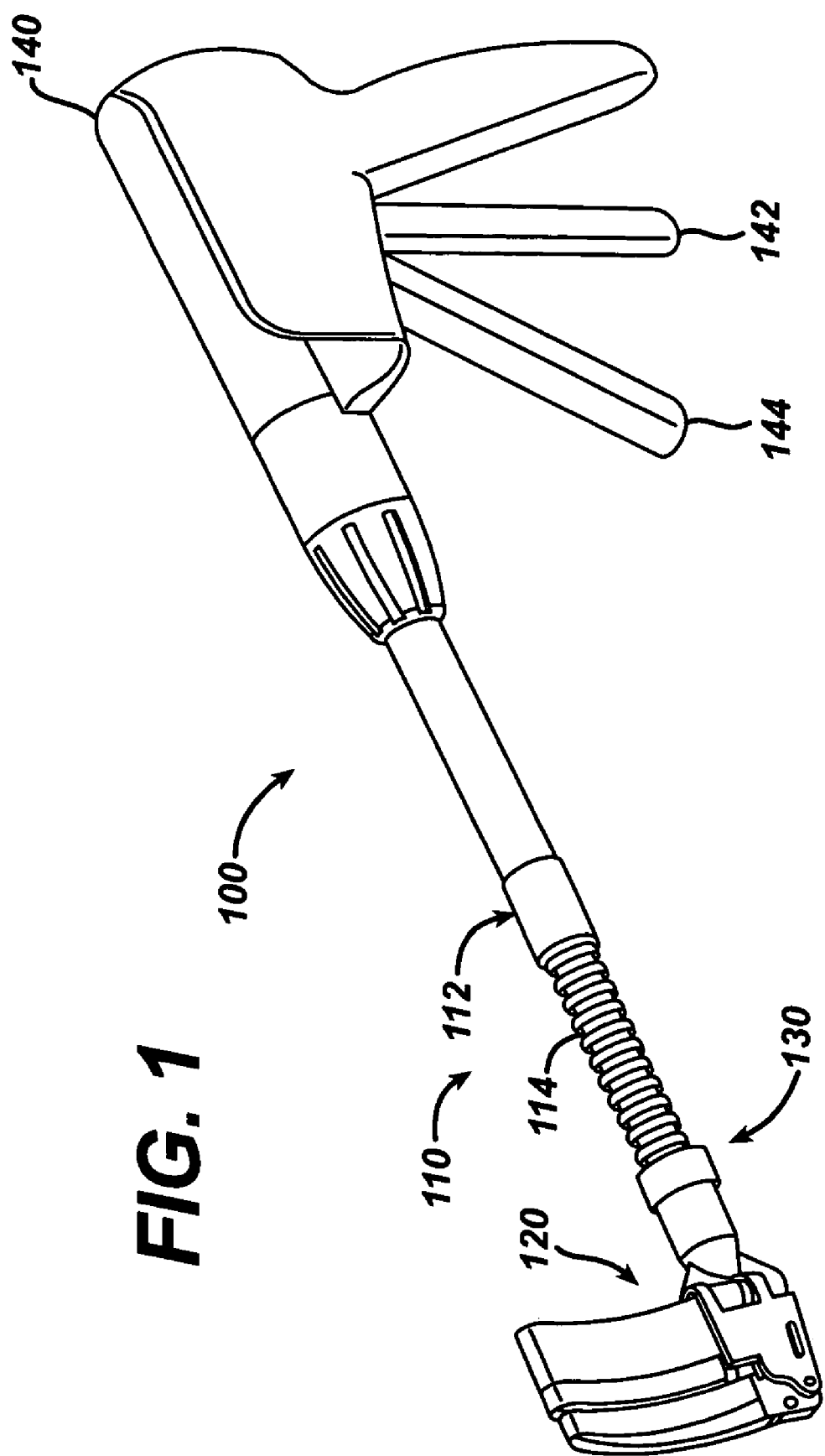
FIG. 1 illustrates a perspective view of a multi-function clamping device according to the invention.

FIG. 1 illustrates a multi-function clamping device according to the invention. The device, shown generally at 100, includes an actuation apparatus or mechanism 110, which can be coupled to a clamping head 120 using a quick connect/ quick release coupling 130. The actuation mechanism 110 includes an elongated portion or elongated body 112, which may include a flexible region or member 114. A handle assembly 140 includes two user-operable portions, such as actuation levers or handles 142 and 144, for triggering, within the handle assembly 140, actuation members that extend to the coupling 130. Many of the features of the actuation mechanism 110 are known in the art and are therefore not shown or discussed specifically herein. For example, the handle assembly 140 and elongated portion 112 may be constructed as discussed in connection with U.S. Pat. No. 5,605,272, "Trigger mechanism for surgical instruments," to Witt et al., issued Feb. 25, 1997, and U.S. Pat. No. 5,452,836, "Surgical stapling instrument with improved jaw closure and staple firing actuator mechanism," to Huitema et al., issued Sep. 26, 1995, both of which are incorporated herein by reference.

The first clamping lever 142 may be rotated about a pivotal mount through an actuation action or stroke to cause a first actuation member 220 (FIG. 3), that extends in the elongated body 112 to the coupling 130, to move linearly inward. The inward or proximal direction is toward the user or the handle assembly 140, while the outward or distal direction is away from the user or handle assembly 140. For example, the first actuation member 220 may include a cable and/or rigid arm that is moved inward as the first lever 142 is moved inward, close to the body of the handle assembly 140. The first actuation member 220 of the actuation mechanism 110 is removably coupled at the coupling 130 to a corresponding actuation member 222 (FIG. 2) in the clamping head 120 to cause a clamping movement in the jaws when the first lever 142 is moved inward. For example, a cable and/or rigid arm in the clamping head 120 may cause one of the jaws to move toward the other jaw, or for both jaws to move toward one another. The jaws may be spring biased toward an open position. In this manner, tissue may be clamped and held between the jaws of the clamping head 120 during a surgical procedure. A spring-loaded ratchet mechanism may be used in the handle assembly 140 to maintain the jaws in the clamped position. A release button in the handle assembly 140 may allow the first lever 142 and spring-loaded ratchet mechanism to be released so that the jaws can return to the open position.

Once the tissue has been clamped in place, the second lever 144 may be moved inward about a pivotal mount through an actuation action to cause a second actuation member 230 (FIG. 3) that extends in the elongated body 112 to the coupling 130 to also move inward. For example, the second actuation member 230 may include a cable and/or rigid arm that is moved inward as the second lever 144 is moved inward. The second actuation member 230 of the actuation mechanism 110 is removably coupled at the coupling 130 to a corresponding actuation member 232 (FIG. 2) in the clamping head 120 to operate the clamping head 120 when the second lever 144 is moved inward. For example, when the clamping head 120 includes a stapler, the actuation member 232 in the clamping head 120 may actuate a staple driving mechanism to fire one or more staples to staple the clamped tissue.

When the clamping head 120 provides ablation electrodes, an on-off switch on the handle assembly 140 may be switched to the on position by the user to energize an electrical supply line 260, 270 (FIG. 3) that extends in the actuation mechanism 110. For example, the electrical supply line 260, 270 may extend from an electrical input jack on the handle assembly 140, to the switch, and through the elongated body 112 to the coupling 130. A generator external to the actuation mechanism 110 may supply any type of energy, such as RF or ultrasound, to the electrical supply line 260, 270 via the jack. A footswitch may be used in place of a switch mounted on the handle assembly 140 if desired. The electrical supply line 260, 270 may be electrically coupled to a corresponding electrical supply line 262, 272 (FIG. 2) in the clamping head 120 using any appropriate type of connector. The electrical supply line 262, 272 in the clamping head 120 in turn is electrically coupled to energize electrodes on the jaws. For example, an anode electrode may be provided on one of the jaws, while a cathode electrode in provided on the other. As discussed further below, the electrodes may be provided using removable electrode holders that can be easily inserted onto, and removed from, the jaws. In another approach, the electrodes may be provided using removable electrode holders that are placed as overlays over the jaws.

Figure 2:
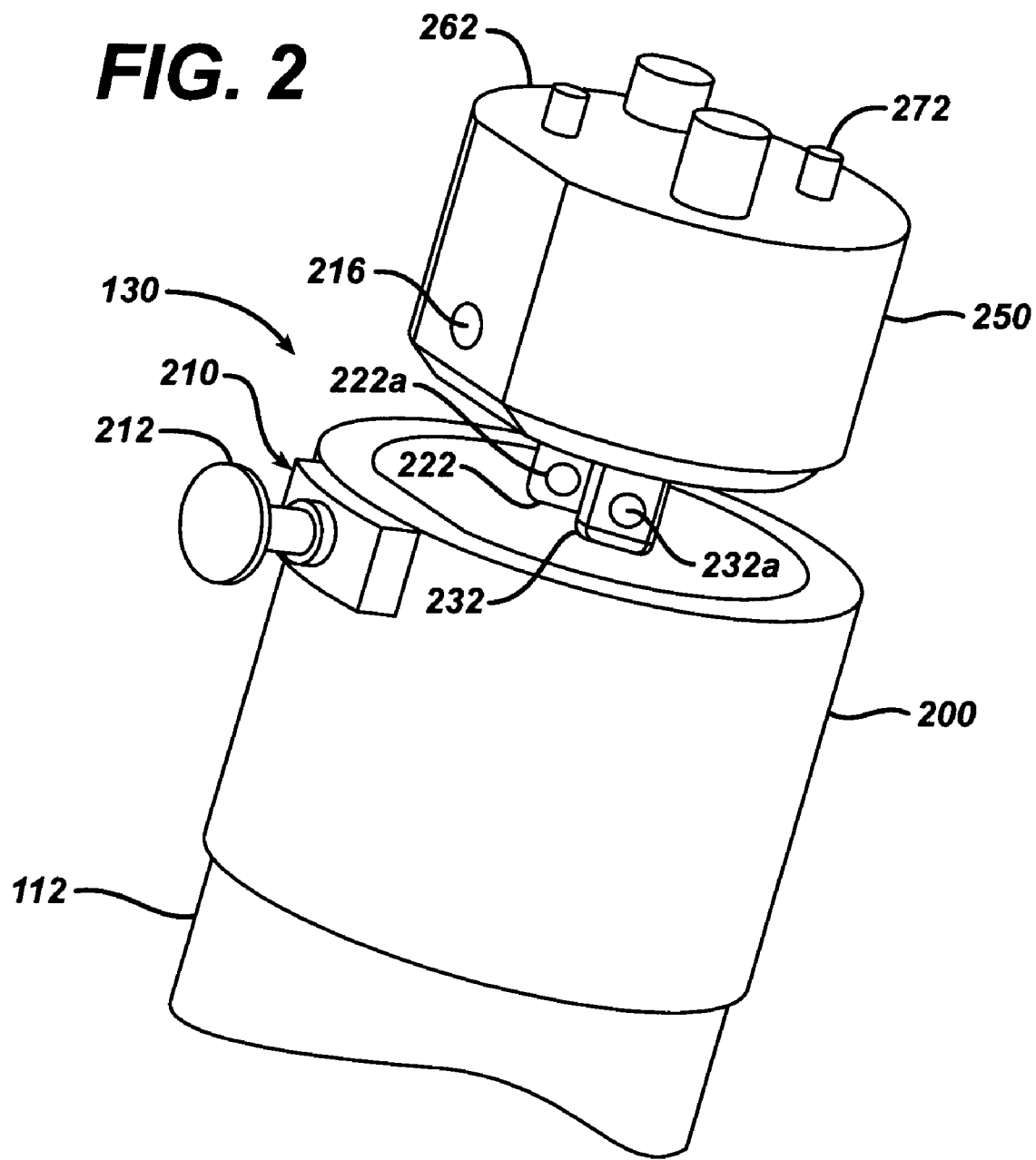
FIG. 2 illustrates an exploded perspective view of a coupling configuration according to the invention.
Figure 3:
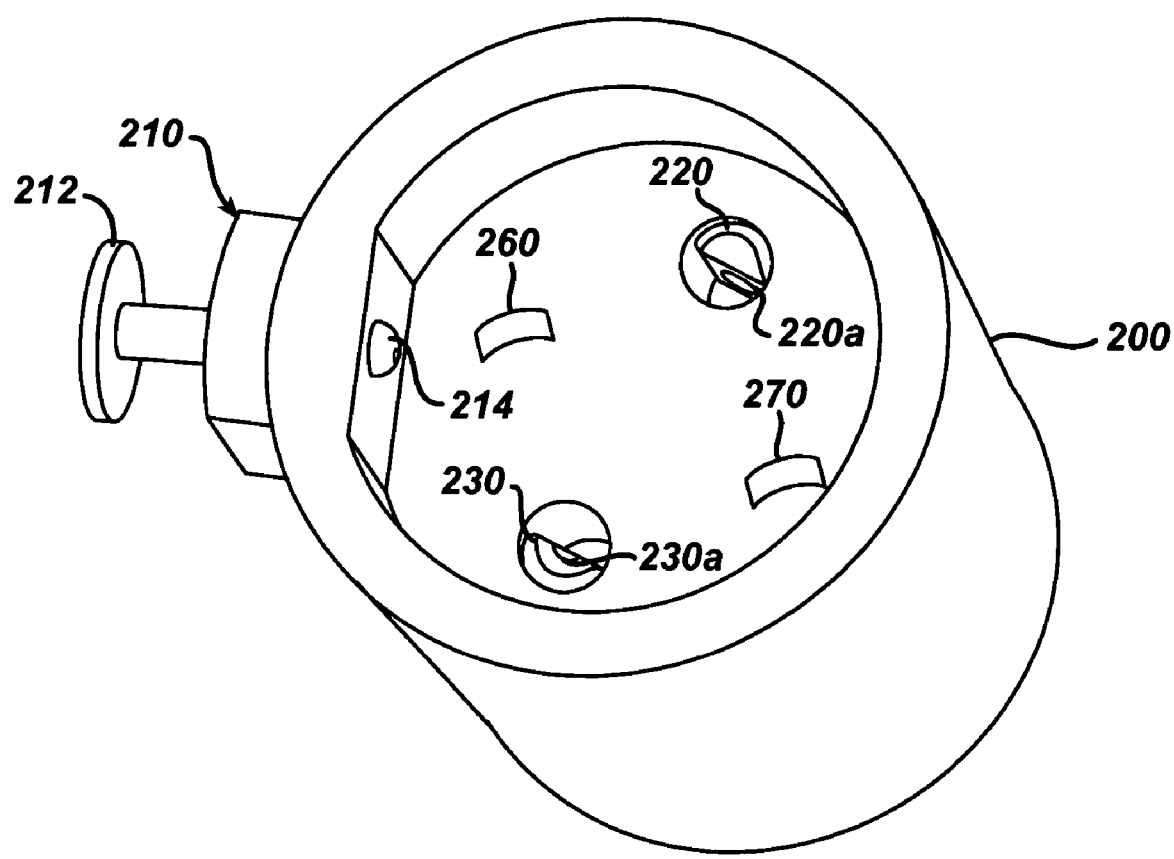
FIG. 3 illustrates a second perspective view of a coupling configuration according to the invention.

FIG. 2 and FIG. 3 illustrate first and second views of a coupling configuration according to the invention. A distal end portion 200 of the elongated body 112 is coupled to a proximal end portion 250 of the clamping head 120 using a quick connect/quick release mechanism 210, which may include a quick release pin or T-handle 212 with spring-loaded locking member 214 and socket 216. The terms "distal" and "proximal" and the like generally refer to the user's viewpoint when operating the device 100. The locking member 214 is spring biased to protrude in an exposed position, as shown in FIG. 3. When the proximal end portion 250 of the clamping head 120 is inserted into the distal end portion 200 of the elongated body 112, the locking member 214, which may be a ball or pin, for instance, mates with the socket 216. The quick release pin 212 may be pulled to retract the locking member 214. The clamping head 120 is thereby securely coupled to the actuation mechanism 110. To release the clamping head 120 and to couple another clamping head to the elongated body 112, the quick release pin 212 is pulled out to withdraw the locking member 214 from the socket 216. Generally, the locking member 214 should be secured in the socket 216 to an extent that the clamping head 120 cannot be manually uncoupled from the actuation mechanism 110, e.g., by pulling on the clamping head 120 but not pulling the pin 212 out.

Additionally, a ball and socket arrangement may be used to couple the respective actuation mechanisms of the actuation mechanism 110 and the clamping head 120. For example, a socket 220a of the first actuation member 220 of the actuation mechanism 110 may be coupled to a ball 222a of the corresponding actuation member 222 of the clamping head 120, while a socket 230a of the second actuation member 230 of the actuation mechanism 110 may be coupled to a ball 232a of the corresponding actuation member 232 of the clamping head 120. All three ball and socket couplings may therefore be coupled when the proximal end portion 250 of the clamping head 120 is inserted into the distal end portion 200 of the elongated body 112. The actuation members 220 and 230 with sockets may be shaped with sloping surfaces to allow the associated balls to be initially withdrawn into the actuation members 220 and 230 during the insertion. Once the balls are aligned with the sockets of the actuation members 220 and 230, they will protrude out under a spring bias to couple with the respective sockets. Alternatively, the sockets are provided on the actuation members 222 and 232 while the balls are provided on the actuation members 220 and 230. Other variations for providing a quick connect/disconnect coupling will be apparent to those skilled in the art. When the proximal end portion 250 of the clamping head 120 is inserted into the distal end portion 200 of the elongated body 112, the ball and socket couplings of the actuation members remain secured to one another due to the biasing of the balls 222a, 232a into their respective sockets 220a, 230a. When the quick release pin 212 is activated to release the coupling 130, the ball and socket couplings of the actuation members remain can be released from one another by pulling the proximal end portion 250 apart from the distal end portion 200 to overcome the biasing force holding the balls 222a, 232a in their respective sockets 220a, 230a.

One of the actuation members, e.g., 222, of the clamping head extends into a corresponding part of the coupling 130 in the clamping head to activate the clamping movement of the jaws. The other actuation member, e.g., 232, of the clamping head extends into a corresponding part of the coupling 130 in the clamping head to activate another mechanism such as a staple driving mechanism, as applicable.

The electrical supply line in the distal end portion 200 of the elongated body 112 may include two electrical paths 260 and 270 which are coupled to corresponding electrical paths 262 and 272, respectively, in the proximal end portion 250 of the clamping head 120. The electrical paths 262 and 272 provide electric energy to electrodes in the clamping head 120 to generate RF or ultrasound energy depending upon the nature of the electrode (crystal). The electrical paths 262 and 272 may include appropriate contacts that touch corresponding contacts in the underside of the proximal end portion 250 of the clamping head 120 of FIG. 2 when the proximal end portion 250 and distal end portion 200 are coupled. The contacts may be spring biased to ensure that a reliable electrical contact is maintained even after extensive use. The contacts may be soldered or otherwise connected to insulated wires that extend in the clamping head 120 and actuation mechanism 110. The contacts themselves may be secured in position in the proximal end portion 250 of the clamping head 120 and the distal end portion 200 of the elongated body 112 using appropriate recessed or raised structures, adhesives or the like. The electrical connections are also properly insulated from surrounding conductive material, if any.

The invention therefore provides a convenient quick connect/quick release coupling that allows different clamping heads to be quickly and easily installed on a common actuation mechanism. Mechanical actuation members as well as electrical supply lines are coupled at the same time. The need for separate actuation mechanisms for different clamping heads is therefore avoided. Note that while two electrical paths and two actuation members are coupled in the present example, the invention can be adapted for use with other configurations by changing the number of actuation members and electrical paths as needed.

Figure 4:
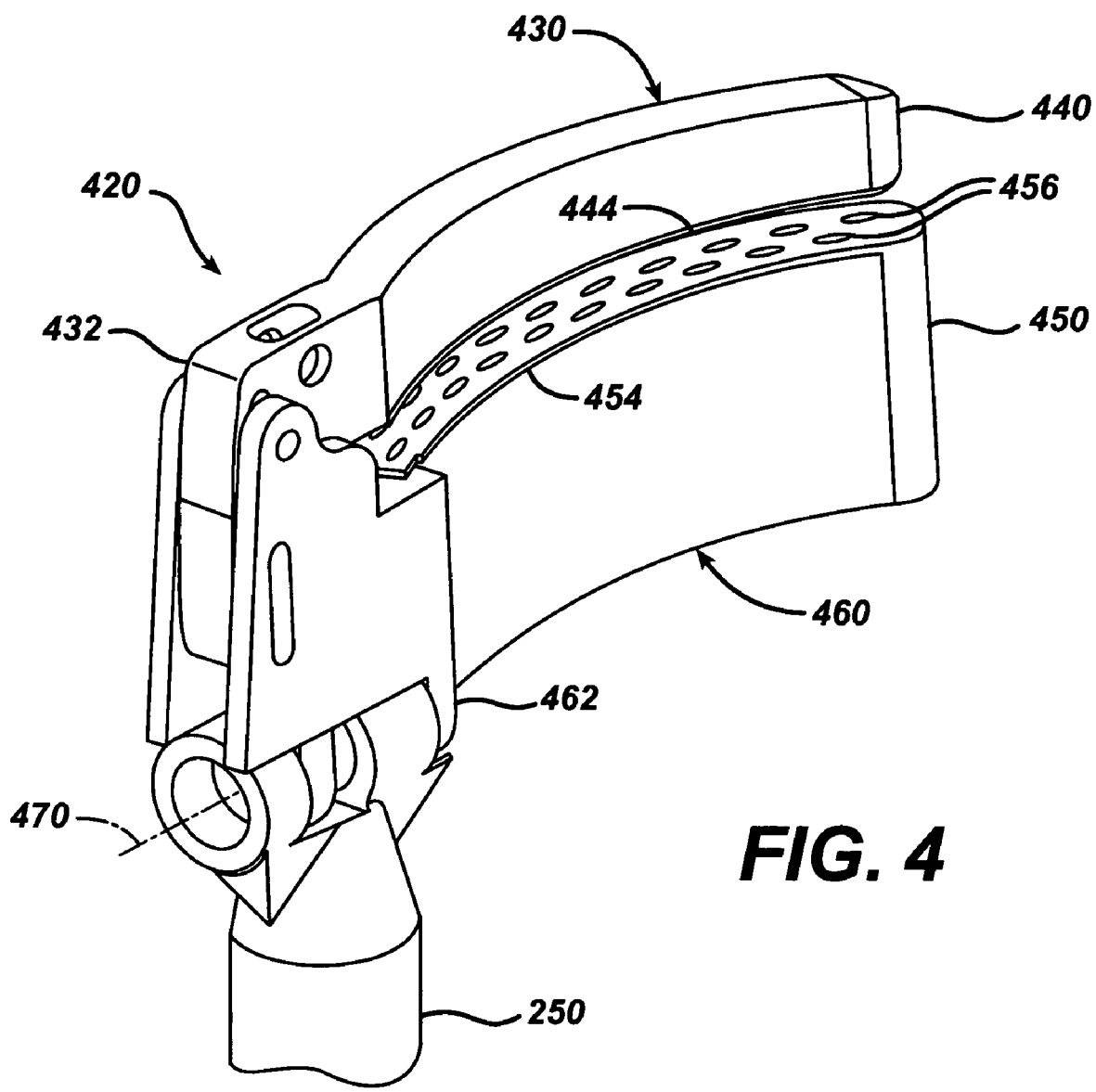
FIG. 4 illustrates a perspective view of a removable staple holder and anvil installed in jaws of a stapler head according to the invention.

FIG. 4 illustrates a removable staple holder installed in a jaw of a stapler head. The jaws can be straight or curved, e.g., arcuate, depending upon the requirement or application. The stapler head 420 includes an upper jaw 430 and lower jaw 460. The upper jaw 430 includes a portion 432 that is mounted for pivoting and/or sliding movement relative to the lower jaw 460, and may be spring biased toward the open position. The lower jaw 460 includes a portion 462 that is mounted to the proximal end portion 250 of the clamping head 120. The portion 462 may pivot about an axis 470. A removable anvil 440 may be installed in the upper jaw 430, while a removable staple holder 450 may be installed in the lower jaw 460. The upper jaw itself can be molded to work as an anvil.

Figure 5:
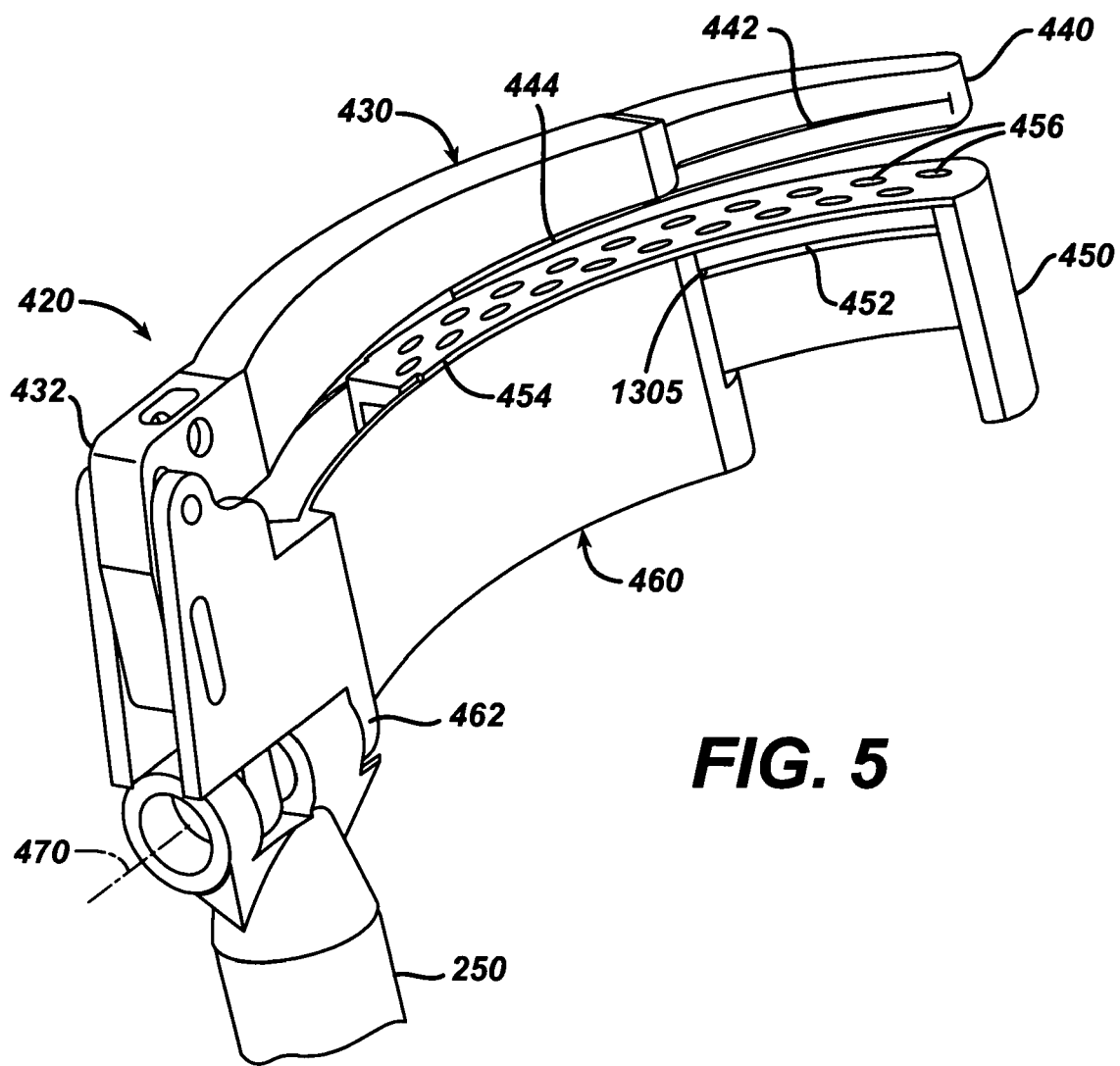
FIG. 5 illustrates a perspective view of a removable staple holder and anvil partially installed in jaws of a stapler head according to the invention.

FIG. 5 illustrates the removable anvil 440 and staple holder 450 in partially installed positions. The anvil 440 and upper jaw 430 include corresponding mating structures that secure the anvil 440 in place while allowing it to be subsequently removed. For example, the anvil 440 may include lengthwise grooves on both sides, e.g., groove 442, while the upper jaw 430 includes corresponding ridges on both interior walls that allow the anvil 440 to be slid into the upper jaw 430 lengthwise. Such ridges may be analogous to the ridges 1305 and 1310 of the lower jaw in FIG. 13. In another approach, the anvil 440 includes ridges, while the upper jaw 430 includes grooves. Various other mating structures will be apparent to those skilled in the art. The anvil 440 may further include flanges on both sides, e.g., flange 444, that abut the lower edges of the upper jaw 430. Such flanges may prevent tissue or fluids from entering the upper jaw 430 during use.

The staple holder 450 includes staple path apertures, e.g., apertures 456, in which staples are stored. In use, the staples are forced from the apertures 456 by a staple driving mechanism. The staples are not shown. The staple holder 450 and lower jaw 460 include corresponding mating structures that secure the staple holder 450 in place while allowing it to be subsequently removed. For example, the staple holder 450 may include lengthwise grooves on both sides, e.g., groove 452, while the lower jaw 460 includes corresponding ridges 1305 and 1310 (FIG. 13) on both interior walls that allow the staple holder 450 to be slid into the lower jaw 460 lengthwise. In another approach, the staple holder 450 includes ridges, while the lower jaw 460 includes grooves. Various other mating structures will be apparent to those skilled in the art. The staple holder 450 may further include flanges on both sides, e.g., flange 454, that abut the upper edges of the lower jaw 460. Such flanges may prevent tissue or fluids from entering the lower jaw 460 during use. The anvil 440 and staple holder 450 may be made of hard material such as stainless steel. for example. Plastics may also be used where possible. Moreover, the upper and lower jaws 430, 460 have corresponding lengthwise profiles, e.g., which may be linear or arcuate.

Figure 6:
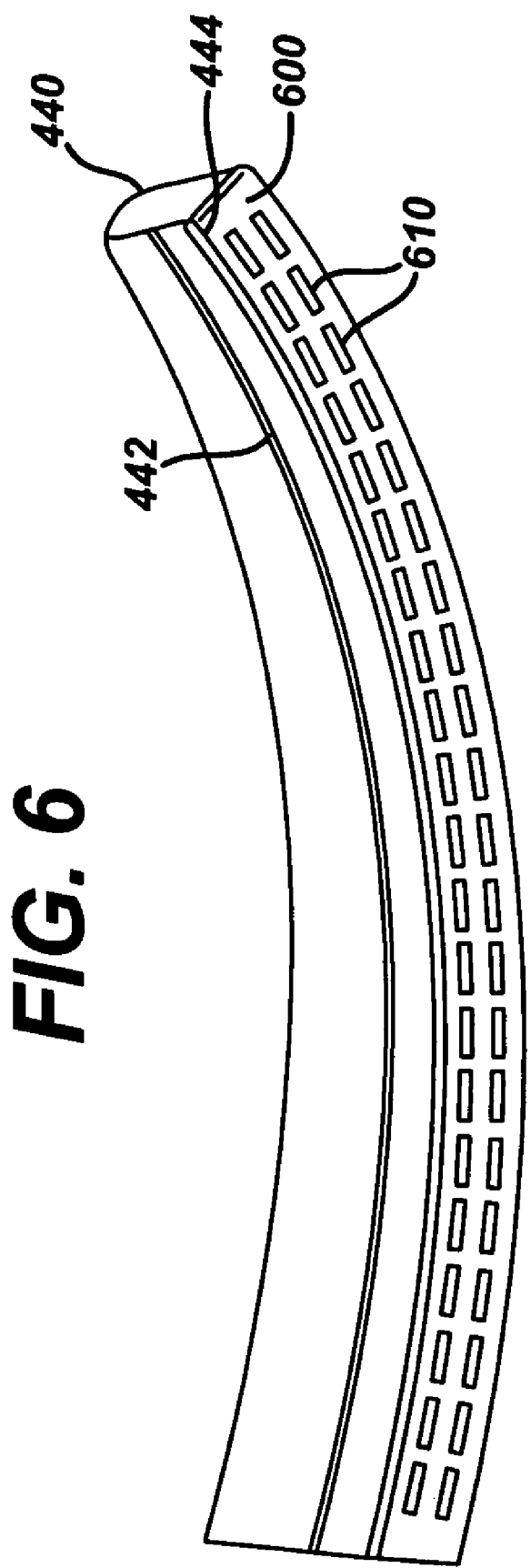
FIG. 6 illustrates a perspective view of a removable anvil for a stapler head according to the invention.

Note that the anvil 440 may be fixed in the upper jaw 430 rather than being removable. This approach still allows different staple holders to be used in the lower jaw, e.g., with different types and sizes of staples, to the extent that the grooves 610 (FIG. 6) in the anvil 440 are compatible with the staples. Moreover, note that the functions of the upper and lower jaws 430, 460 can generally be interchanged, e.g., to provide the staple holder and the staple driving mechanism in the upper jaw, and the anvil in the lower jaw. FIG. 6 illustrates the removable anvil 440. A bottom face 600 of the anvil 440 includes a number of staple forming grooves, e.g., grooves 610, according to the arrangement of staples in the staple holder 450. An anvil 440 with a particular arrangement of grooves may be used based on the type of staples and staple holder used, e.g., to accommodate different staple heights, widths, pitches, materials and so forth.

Figure 7:
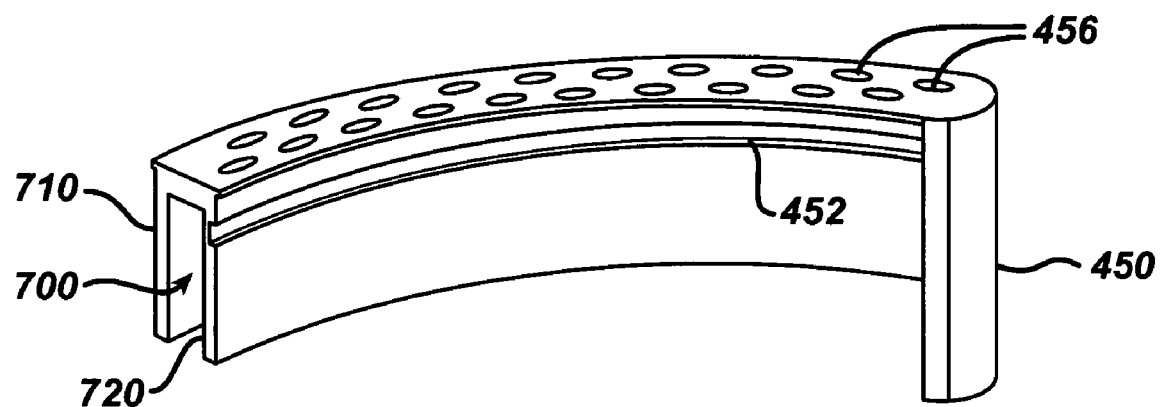
FIG. 7 illustrates a perspective view of a removable staple holder for a stapler head according to the invention.

FIG. 7 illustrates the removable staple holder 450, including the staple path apertures 456 and groove 452. A cutout region 700 may be provided to mount or locate the staple driving mechanism between the side walls 710 and 720.

Figure 8:
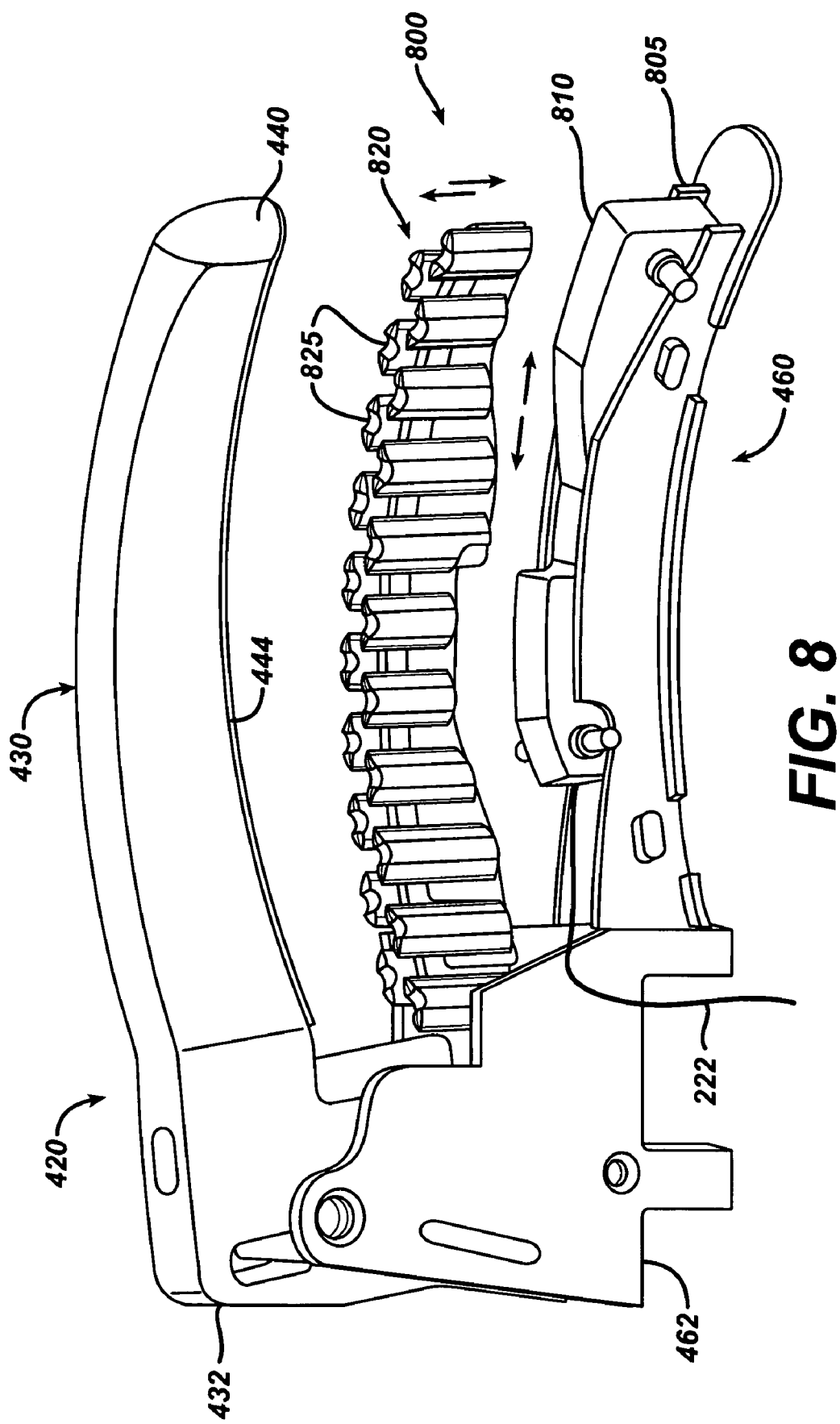
FIG. 8 illustrates an exploded perspective view of a staple driving mechanism in a jaw of a stapler head according to the invention.

FIG. 8 illustrates a first view of a staple driving mechanism in a jaw of a stapler head according to the invention. The staple driving mechanism 800 may include a cam 805 formed as dual shaped walls. A cam follower 810 travels along the cam 805 from right to left horizontally when the actuation member 222 such as a cable is moved responsive to the second lever 144 of the actuation mechanism 110. The cam follower 810 may be spring biased to the initial, rightmost position, to which it returns after the staples are fired. A staple pusher mechanism 820 includes individual staple pushers, e.g., 825, for firing each of the staples through the staple path apertures 456 and into the tissue clamped between the jaws 430, 460. Note that the staple pusher mechanism 820 is shown above the cam 805 for clarity, but in practice is located proximate to the cam 805 and within the lower jaw 460. The walls of the lower jaw 460 also are not shown for clarity.

Figure 9:
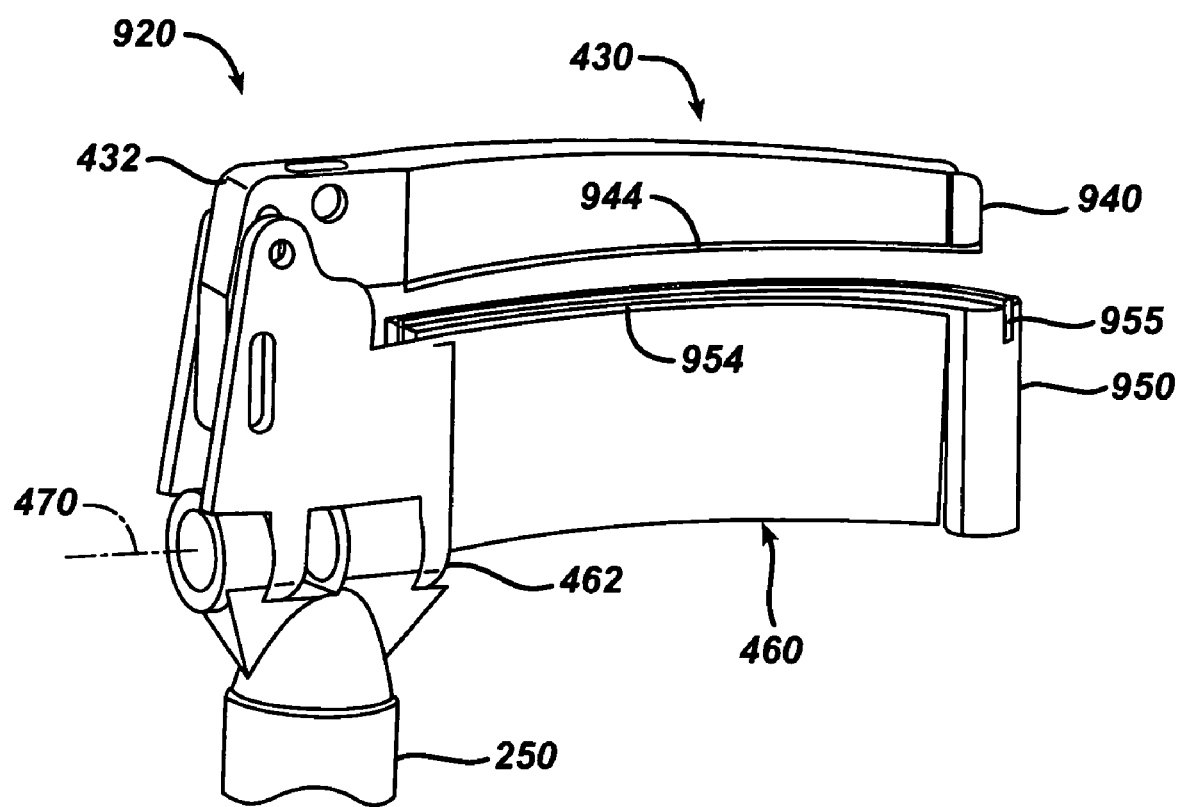
FIG. 9 illustrates a perspective view of removable electrode holders installed in jaws of an ablation head according to the invention.

FIG. 9 illustrates removable electrode holders installed in jaws of an ablation head according to the invention. The ablation head 920 is analogous to the stapler head 420 of FIG. 4, but instead of an anvil, an electrode holder 940 (a first electrode holder is installed in the upper jaw 430, while a corresponding electrode holder 950 (a second electrode holder) with electrode 955 (a second electrode) is installed in the lower jaw 460. One of the electrodes can serve as a cathode electrode, while the other can serve as an anode electrode. The electrodes are electrically coupled to the electrical supply lines 262, 272 in the clamping head 920 and to the electrical supply lines 260, 270 in the actuation mechanism 110, so that the user can selectively apply an energy to tissue that is clamped between the jaws 430 and 460, thereby ablating the tissue as desired for a surgical procedure. The electrode holder 940 may include flanges on both sides, e.g., flange 944, tat rest on the lower edges of the upper jaw 430 to prevent the influx of tissue or fluids into the upper jaw 430. Similarly, the electrode holder 950 may include flanges on both sides, e.g., flange 954, that rest on the upper edges of the lower jaw 460 to prevent the influx of tissue or fluids into the lower jaw 460.

Figure 10:
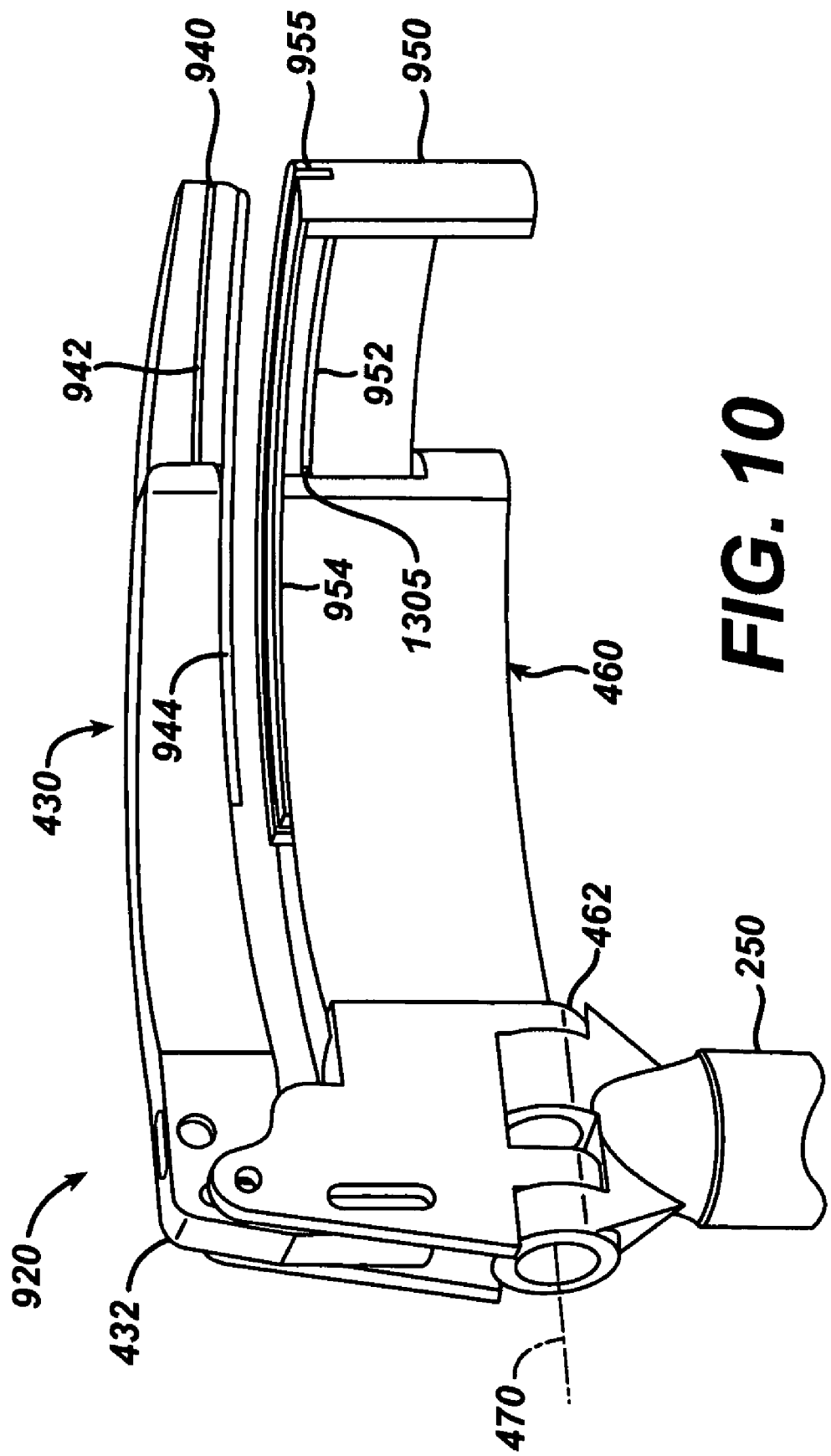
FIG. 10 illustrates a perspective view of removable electrode holders partially installed in jaws of an ablation head according to the invention.

FIG. 10 illustrates removable electrode holders partially installed in jaws of the ablation head 920 according to the invention. The electrode holder 940 and upper jaw 430 include corresponding mating structures that secure the electrode holder 940 in place while allowing it to be subsequently removed. For example, the electrode holder 940 may include lengthwise grooves on both sides, e.g., groove 942, while the upper jaw 430 includes corresponding ridges on both interior walls that allow the electrode holder 940 to be slid into the upper jaw 430 lengthwise. Such ridges may be analogous to the ridges 1305 and 1310 of the lower jaw in FIG. 13. In another approach, the electrode holder 940 includes ridges, while the upper jaw 430 includes grooves. Various other mating structures will be apparent to those skilled in the art.

In the lower jaw 460, the electrode holder 950 includes the electrode 955. The electrode 955 may extend centrally along the length of the electrode holder 950, although other electrode configurations may be used as well, such as a dual electrodes, a curved or zig-zag shaped electrode, and so forth. Different electrode thicknesses and materials may be used as well. The invention allows a specific type of electrode to be quickly installed in the upper and/or lower jaws to optimize the ablation process. The electrode holder 950 and lower jaw 460 include corresponding mating structures that secure the electrode holder 950 in place while allowing it to be subsequently removed. For example, the electrode holder 950 may include lengthwise grooves on both sides, e.g., groove 952, while the lower jaw 460 includes corresponding ridges 1305 and 1310 (see also FIG. 13) on both interior walls that allow the electrode holder 950 to be slid into the lower jaw 460 lengthwise. In another approach, the electrode holder 950 includes ridges, while the lower jaw 460 includes grooves. Various other mating structures will be apparent to those skilled in the art.

The electrode holders 940 and 950 may be formed of a non-conductive material such as plastic, for example, while the electrodes are formed from a conductive material such as metal. Note that one or both of the electrodes may be fixed rather than removable. Where one electrode is fixed, different electrodes can still be used in the opposing jaw.

Figure 11:
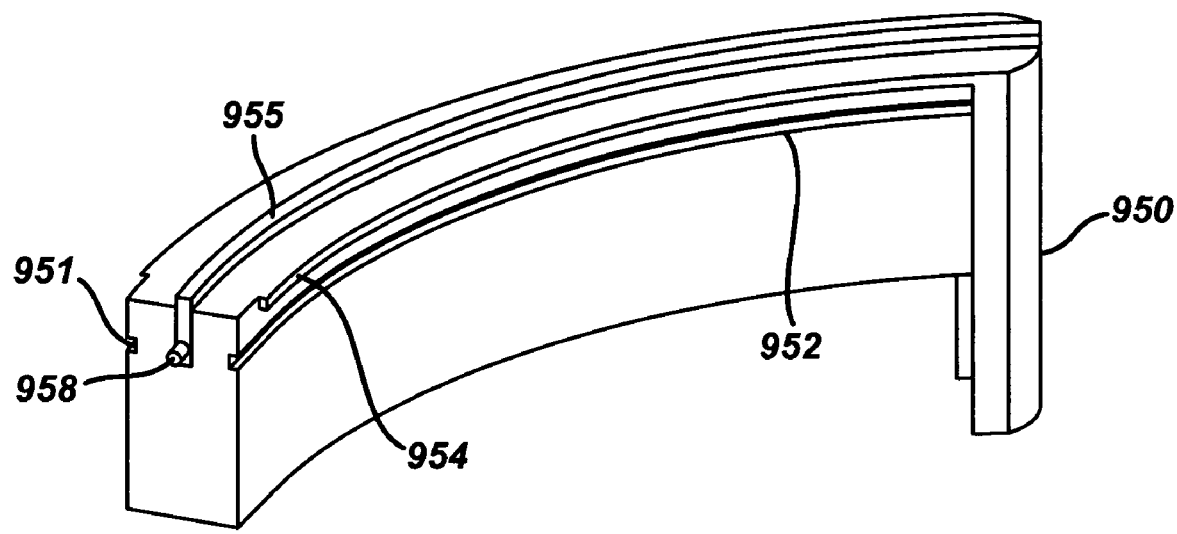
FIG. 11 illustrates a perspective view of an electrode holder for a lower jaw of an ablation head according to the invention.

FIG. 11 illustrates the electrode holder 950 for the lower jaw 460 of the ablation head 920, including the electrode 955, flanges 954 and 956, and groove 952. A portion of the groove 951 on the opposing side of the electrode holder 950 is visible as well. The electrode 955 includes a connecting portion or electrical contact 958 (a fourth electrical contact) that is electrically coupled with an electrical supply path in the clamping head 920, such as the electrical path 262 of FIG. 2. For example, the connecting portion 958 may be electrically coupled with an electrical contact 1320 (FIG. 13) of the lower jaw when the electrode holder 950 is installed in the lower jaw 460. In one possible design, the connecting portion 958 is a protruding member as shown, and the electrical contact 1320 (a second electrical contact) is a socket that is electrically coupled to the electrical path 262 of FIG. 2 by wiring internal to the clamping head 920. The socket may comprise any appropriate design that provides a reliable electrical connection while allowing the connecting portion 958 to be subsequently removed. For example, the socket may include resilient arms that are pushed apart when the connecting portion 958 is inserted. The electrical connection between the connecting portion 958 and the socket is electrically insulated from surrounding material, such as the jaw 460, which may be formed of metal.

Figure 12:
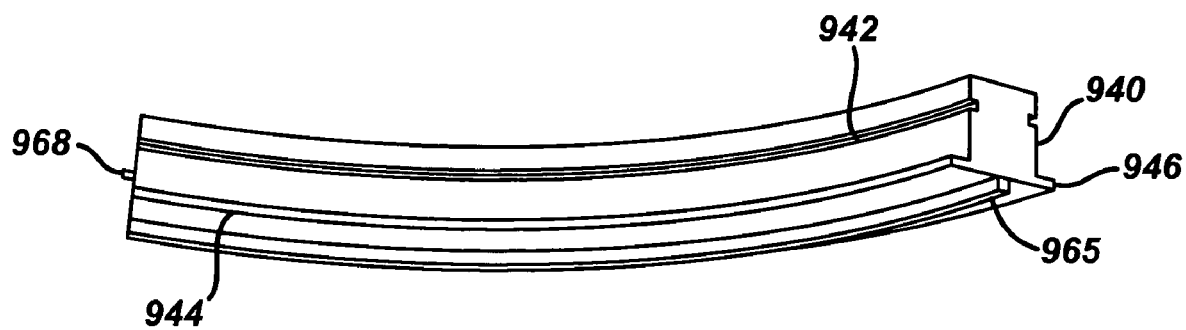
FIG. 12 illustrates a perspective view of an electrode holder for an upper jaw of an ablation head according to the invention.

FIG. 12 illustrates the electrode holder 940 for the upper jaw 430 of the ablation head 920, including an electrode 965 (a first electrode), flanges 944 and 946, and groove 942. The electrode 965 includes a connecting portion or electrical contact 968 (a third electrical contact) that is electrically coupled with an electrical supply path in the clamping head 920, such as the electrical path 272 of FIG. 2. For example, the connecting portion 968 may be electrically coupled with an electrical contact (a first electrical contact) analogous to the electrical contact 1320 (FIG. 13) of the lower jaw when the electrode holder 940 is installed in the upper jaw 430. The discussion above regarding the electrode holder 950 for the lower jaw 460 applies analogously to the electrode holder 940 for the upper jaw 430.

Figure 13:
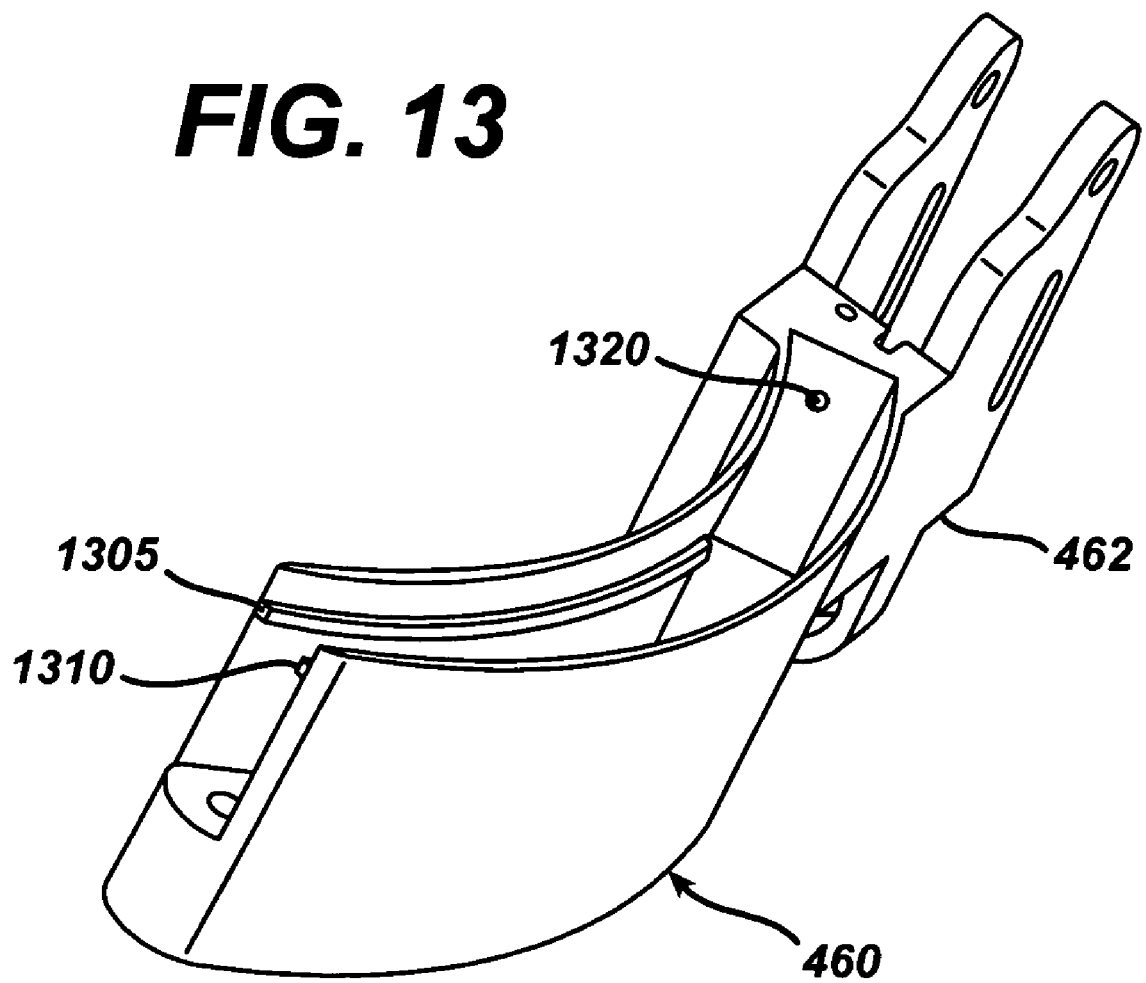
FIG. 13 illustrates a perspective view of a lower jaw of a clamping head for receiving an electrode holder or staple holder according to the invention.

FIG. 13 illustrates the lower jaw 460 of a clamping head for receiving an electrode holder or staple holder according to the invention. The lower jaw 460 is shown in isolation with the portion 462. As discussed, the lower jaw 460 may include a mating structure such as ridges 1305 and 1310 that mate with corresponding structures in the removable component. An electrical contact 1320 electrically couples the electrode in an electrode holder to an electrical supply line. Note that the electrical contact 1320 and electrical supply line are not used when the clamping head is configured for stapling. However, the invention advantageously enables the same clamping head to be configured in turn for both stapling and ablation, thereby avoiding the need for completely separate devices.

Figure 14:
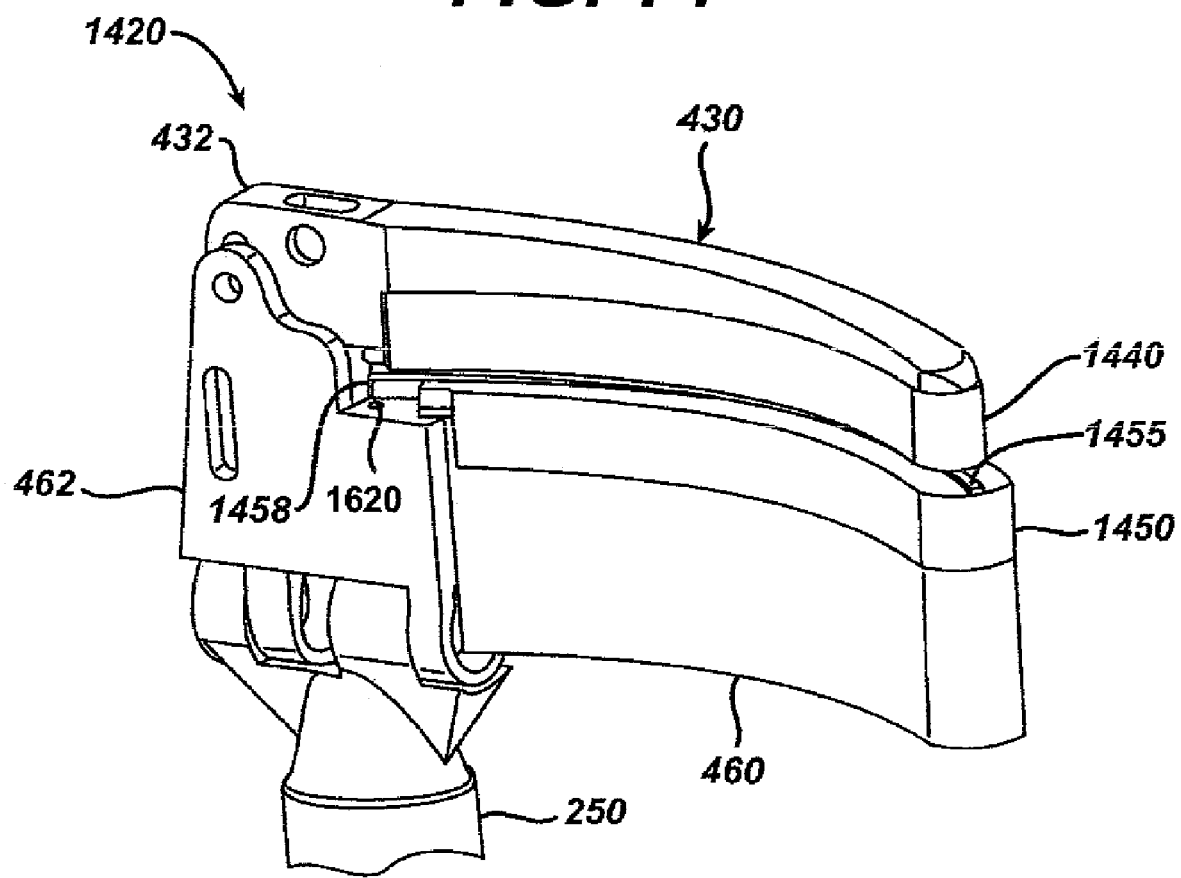
FIG. 14 illustrates a perspective view of a clamping head with electrode holder overlays for its jaws according to the invention.
Figure 15:
FIG. 15 illustrates a perspective view of an electrode holder overlay for a lower jaw according to the invention.

FIG. 14 illustrates a clamping head 1420 with electrode holder overlays 1440 and 1450 for its jaws 430 and 460, respectively. For example, the clamping head 1420 may be configured as a stapler with an anvil in the upper jaw 430 and a stapling mechanism in the lower jaw 460. The present invention reconfigures the clamping head 1420 to an ablation head quickly and easily without the need for uncoupling the proximal end portion 250 from the distal end portion 200. Here, the electrode overlay 1440 is provided over the upper jaw 430, and the electrode overlay 1450 is provided over the lower jaw 460. The electrode overlays 1440 and 1450 maybe form-fitting plastic structures that are secured over the respective jaws, such as by using a snap fit. Corresponding mating structures such as groove and ridge may be used to secure the overlays on the jaws. For example, the overlays may be pushed lengthwise over the jaws. Or, the overlays may be pushed downward onto the lower jaw 460 and upward onto the upper jaw 430. Each overlay includes an electrode that is electrically coupled to an electrical supply line in the clamping head 1420 when the overlay is installed on the respective jaw. For example, the electrode overlay 1450 includes an electrode 1455 and electrical contact 1458 that is electrically coupled to an electrical contact 1620 in the portion 462. The electrical contact 1458 may include a protruding member that extends into a socket that forms the electrical contact 1620. The electrical contact 1620 maybe electrically coupled with an electrical supply path in the clamping head 1420, such as the electrical path 262 of FIG. 2. An analogous arrangement may be made for the upper electrode overlay 1440 to electrically couple its electrode to an electrical supply path in the clamping head 1420, such as the electrical path 272 of FIG. 2. Various other arrangements for electrically coupling the electrodes will be apparent to those skilled in the art. FIG. 15 illustrates the electrode holder overlay 145 for the lower jaw 460, including the electrode 1455 and electrical contact 1458, in further detail. The electrode overlays 1440 and 1450 may be used with a device that does not have a removable staple holder or anvil, or quick connect/disconnect clamping head in which case the overlays 1440, 1450 can be used to quickly convert a conventional stapler device (configured to accept such overlays) into an ablation device.

Note that in the various embodiments discussed, the mating structures or other structures may be configured with sensors to provide a visible and/or audible indication that the removable component that is being installed in the jaw, e.g., electrode holder, anvil, or staple holder, has been fully installed in the proper position. For example, known structures or sensors may be used that cause an audible click to be heard when the component is fully seated in the jaw. Additionally, further constructs may be provided to lock the components in place in the jaw while permitting subsequent removal.

The present invention has been described herein with reference to certain preferred embodiments. These embodiments are offered as illustrative, and not limiting, of the scope of the invention. Certain modifications or alterations may be apparent to those skilled in the art without departing from the scope of the invention, which is defined by the appended claims.

What is claimed is:

1. An actuation mechanism, comprising:
a handle assembly including at least a first user-operable portion;
an elongated body extending distally from the handle assembly;
a first actuation member carried within the elongated body and extending to a distal end of the elongated body;
wherein the first actuation member is moveable in response to movement of the first user-operable portion;
an electrical supply line extending from the handle assembly to the distal end of the elongated body; and
a coupling at the distal end of the elongated body for releasably coupling the elongated body in turn to a clamping head and an electrically-energizable head;
wherein, when the elongated body is coupled to the clamping head, the first actuation member controls clamping of the clamping head, and when the elongated body is coupled to the electrically-energizable head, the electrical supply line electrically energizes the electrically-energizable head.

2. The actuation mechanism of claim 1, wherein: the clamping head comprises a stapler.

3. The actuation mechanism of claim 1, wherein the handle assembly includes a second user-operable portion, and the clamping head comprises a stapler with a staple driving mechanism, the actuation mechanism further comprising:
a second actuation member carried within the elongated body and extending to a distal end of the elongated body;
wherein the second actuation member is moveable in response to movement of the second user-operable portion for controlling firing of staples in the staple driving mechanism.

4. The actuation mechanism of claim 1, wherein:
the coupling comprises a quick connect/quick release coupling.

5. The actuation mechanism of claim 1, wherein:
the coupling comprises a ball and socket coupling.

6. The actuation mechanism of claim 1, wherein:
the electrically-energizable head comprises an ablation head.

7. The actuation mechanism of claim 6, wherein:
the first actuation mechanism controls clamping of jaws of the ablation head.

8. An ablation device, comprising:
a first jaw including a first electrode;
a second jaw having a proximal end and including a second electrode, the second jaw operatively associated with the first jaw and opposing the first jaw;
an actuation mechanism releasably coupled to the proximal end of the second jaw;
a first actuation member responsive to the actuation mechanism, and extending from the proximal end of the second jaw for causing a clamping movement of the first and second jaws, wherein the proximal end of the second jaw comprises a quick connect/quick release coupling; and
an electrical supply line responsive to the actuation mechanism, and extending from the proximal end of the second jaw for electrically energizing the first and second electrodes.

9. The ablation device of claim 8, wherein:
the proximal end of the second jaw comprises a ball and socket coupling for releasably coupling to the actuation mechanism.

10. A clamping ablation head, comprising:
a first jaw having an associated first electrode;
a second jaw operatively associated with the first jaw, opposing the first jaw, and including an electrical contact; and
an electrode holder holding a second electrode; wherein
the electrode holder is removably receivable by the second jaw; and
the second electrode includes an electrical contact that is electrically coupled to the electrical contact of the second jaw when the electrode holder is received by the second jaw.

11. The clamping ablation head of claim 10, further comprising:
a first actuation member responsive to an actuation mechanism for causing a clamping movement of the first and second jaws; and
an electrical supply line responsive to the actuation mechanism for electrically energizing the first and second electrodes.

12. The clamping ablation head of claim 10, wherein:
the first and second electrodes extend substantially arcuately along respective lengths of the first and second jaws, respectively.

13. The clamping ablation head of claim 10, further comprising:
a proximal end on which the second jaw is carried for releasably coupling to a distal end of the actuation mechanism.

14. The clamping ablation head of claim 13, wherein:
the proximal end comprises a quick connect/quick release coupling.

15. The clamping ablation head of claim 10, wherein:
the electrode holder and second jaw have corresponding mating structures by which the electrode holder is removably received by the second jaw.

16. The clamping ablation head of claim 10, wherein:
the first electrode is carried by a further electrode holder that is removably receivable by the first jaw; and
the first electrode includes an electrical contact that is electrically coupled to an electrical contact of the first jaw when the further electrode holder is received by the first jaw.

17. An ablation head, comprising:
a first jaw having a first electrical contact and a second jaw having a second electrical contact;
a first electrode holder and a second electrode holder removably receivable by the first jaw and the second jaw, respectively;
a first electrode comprising a third electrical contact, the first electrode carried by the first electrode holder; and
a second electrode comprising a fourth electrical contact, the second electrode carried by the second electrode holder;
wherein the first and second contacts of the first and second jaws are respectively electrically coupled to the third and fourth contacts of the first and second electrodes when the first and second electrode holders are received by the first and second jaws.

18. The ablation head of claim 17, wherein:
one of the first and second electrodes is a cathode electrode, and the other of the first and second electrodes is an anode electrode.

19. The ablation head of claim 17, wherein: the first and second electrode holders have mating structures corresponding mating structures of the first and second jaws, respectively, enabling the first and second electrode holders to be removably received by the first and second jaws, respectively.

20. A combination stapler and ablation head, comprising:
a first jaw including an anvil;
a second jaw operatively associated with the first jaw, opposing the first jaw and including a staple driving mechanism; and
a staple holder operatively associated with the second jaw, wherein the staple holder is actuable by the staple driving mechanism, and includes a staple supply;
an electrode holder; and
an electrode carried by the electrode holder and including an electrical contact;
wherein the electrode holder is removably receivable by at least one of the first and second jaws such that the electrical contact of the electrode is electrically coupled to an electrical contact of the at least one of the first and second jaws.

21. The combination stapler and ablation head of claim 20, wherein:
the electrode holder and the at least one of the first and second jaws have corresponding mating structures by which the electrode holder is removably received by the at least one of the first and second laws.

22. The combination stapler and ablation head of claim 20, wherein:
the electrode holder is provided as an overlay of the at least one of the first and second jaws.

23. A clamping device, comprising:
a handle assembly including first and second user-operable portions; an elongated body extending distally from the handle assembly;
first and second actuation members carried within the elongated body and extending to a distal end of the elongated body;
wherein the first actuation member is moveable in response to movement of the first user-operable portion, and the second actuation member is movable in response to movement of the second user-operable portion;
an electrical supply line extending from the handle assembly to the distal end of the elongated body;
a coupling at the distal end of the elongated body; and
a clamping head comprising a first jaw, and a second jaw operatively associated with the first jaw and opposing the first jaw, the second jaw having a proximal end configured to releasably couple to the coupling at the distal end of the elongated body;
wherein the clamping head is actuable by the first and second actuation members.

24. The clamping device of claim 23, wherein:
the proximal end of the second jaw and the coupling at the distal end of the elongated body form a quick connect/quick release coupling.

* * * * *